(12) United States Patent
Patil

(10) Patent No.: US 6,854,601 B2
(45) Date of Patent: Feb. 15, 2005

(54) BACTERIOSTATIC FILTER CARTRIDGE

(75) Inventor: Arvind S. Patil, Davidson, NC (US)

(73) Assignee: Microban Products Company, Huntersville, NC (US)

( * ) Notice: Subject to any disclaimer, the term of this patent is extended or adjusted under 35 U.S.C. 154(b) by 323 days.

(21) Appl. No.: 09/946,031

(22) Filed: Sep. 4, 2001

(65) Prior Publication Data
US 2002/0043493 A1 Apr. 18, 2002

Related U.S. Application Data

(63) Continuation-in-part of application No. 09/181,358, filed on Oct. 28, 1998, now Pat. No. 6,283,308, which is a continuation-in-part of application No. 08/877,080, filed on Jun. 17, 1997, now Pat. No. 5,868,933, which is a continuation-in-part of application No. 08/573,067, filed on Dec. 15, 1995, now Pat. No. 5,762,797.

(51) Int. Cl.[7] .............................................. B01D 27/08
(52) U.S. Cl. ....................... 210/484; 210/488; 210/489; 210/493.1; 210/483.5; 210/494.1
(58) Field of Search ................................ 210/484, 488, 210/489, 493.1, 493.5, 494.1, 497.1, 494.2

(56) References Cited

U.S. PATENT DOCUMENTS

| | | | |
|---|---|---|---|
| 3,065,856 A | * | 11/1962 | Goldman |
| 3,953,545 A | * | 4/1976 | Stoy ............................ 525/196 |
| 4,032,688 A | * | 6/1977 | Pall ............................ 428/36.1 |
| 4,048,078 A | * | 9/1977 | Allen ........................... 507/202 |
| 5,006,267 A | * | 4/1991 | Vaughn et al. ............... 210/755 |
| 5,071,551 A | * | 12/1991 | Muramatsu et al. ......... 210/266 |
| 5,102,547 A | * | 4/1992 | Waite et al. ................. 210/501 |
| 5,180,585 A | * | 1/1993 | Jacobson et al. ............ 424/405 |
| 5,594,070 A | * | 1/1997 | Jacoby et al. ................. 525/88 |
| 5,709,870 A | * | 1/1998 | Yoshimura et al. .......... 424/404 |
| 5,762,797 A | * | 6/1998 | Patrick et al. ............ 210/497.1 |
| 5,868,933 A | * | 2/1999 | Patrick et al. ............... 210/484 |
| 6,283,308 B1 | * | 9/2001 | Patil et al. ................... 210/484 |
| 6,551,608 B2 | * | 4/2003 | Yao ............................. 424/409 |

FOREIGN PATENT DOCUMENTS

JP 57-84703 * 5/1982

* cited by examiner

Primary Examiner—Ana Fortuna
(74) Attorney, Agent, or Firm—Stan Baker

(57) ABSTRACT

A bacteriostatic filter cartridge having a porous core member about which is layered a yarn and/or a polyester membrane and/or melt blown web of polypropylene and/or a trilaminate polypropylene membrane, any or all of which may be impregnated with an antimicrobial agent. The filter cartridge is sized so as to fit tightly into a cartridge housing of a fluid filtration system. Fluid passing through the cartridge housing will be filtered by the filter cartridge to remove contaminants from the water and which prevents the growth of bacterial and other microorganisms on the filter media.

17 Claims, 5 Drawing Sheets

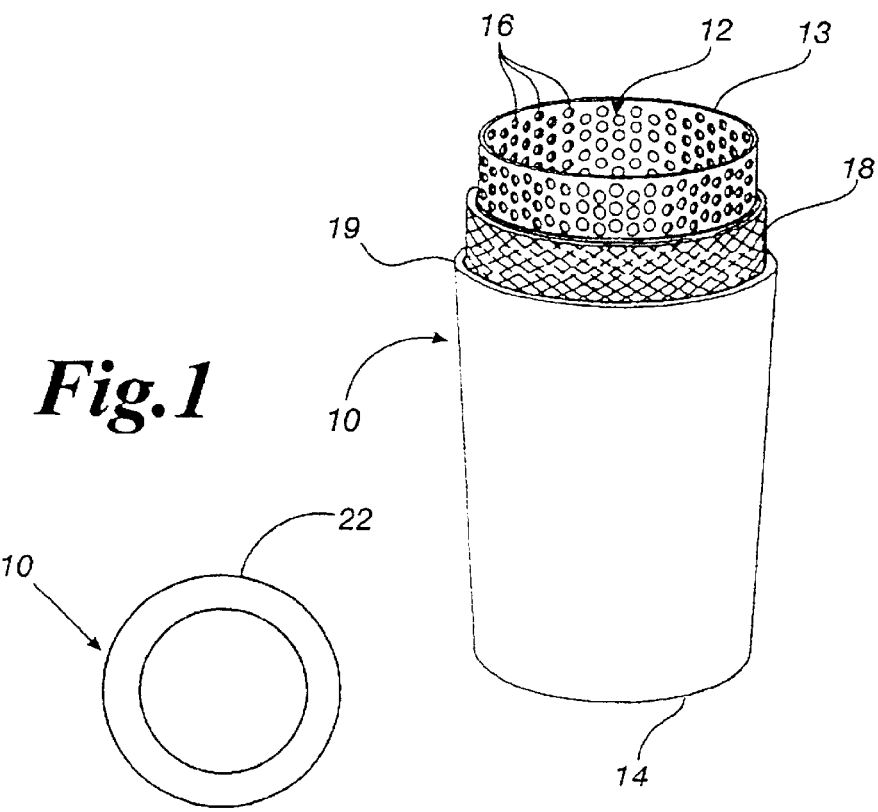
Fig.1
Fig.3
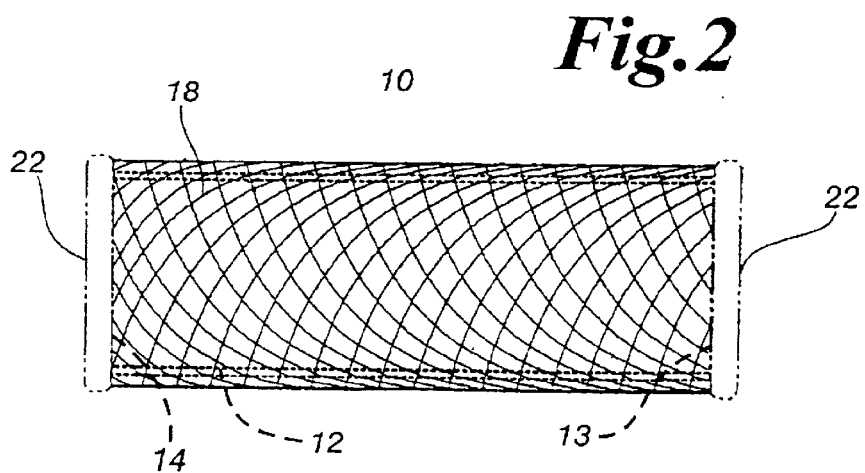
Fig.2

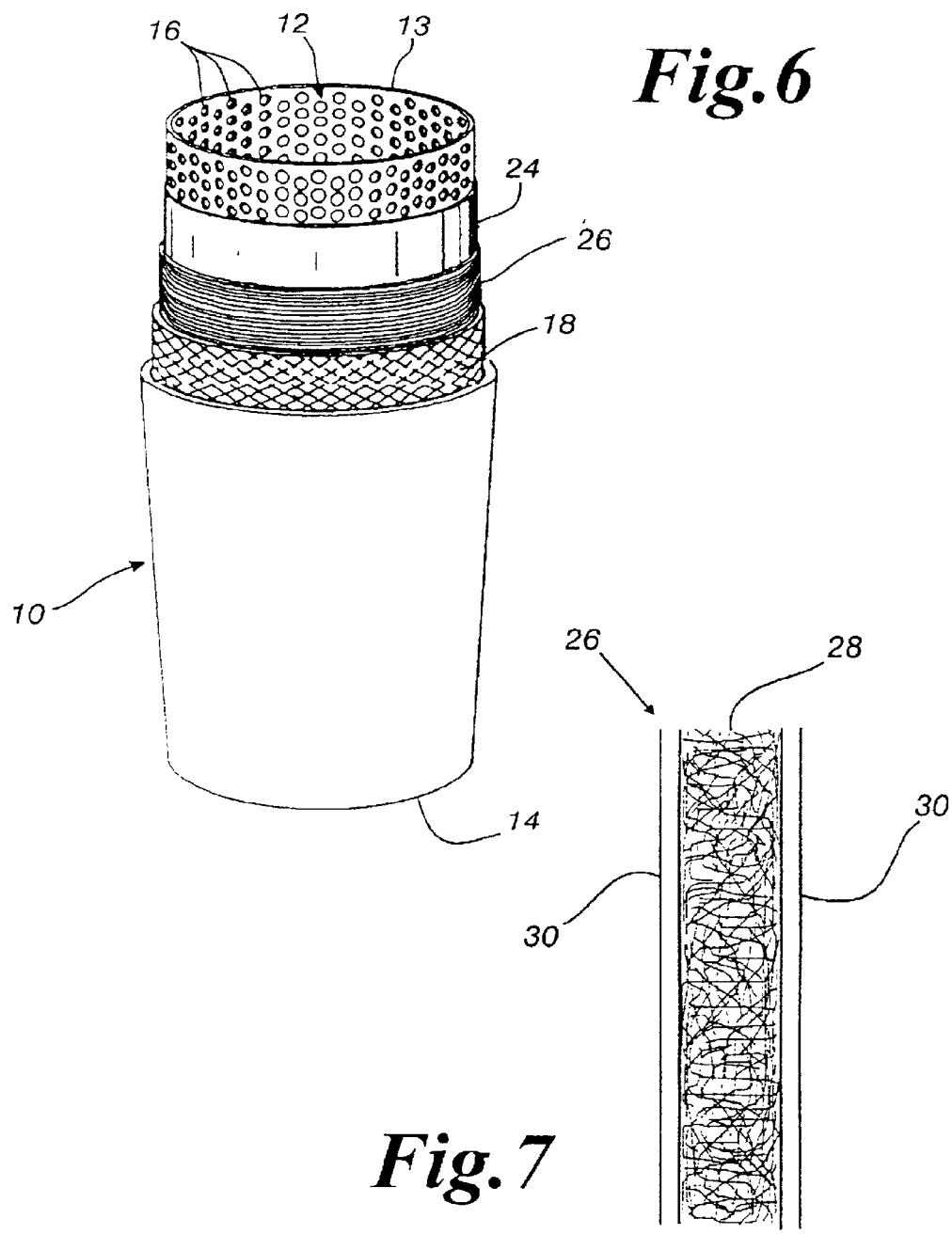

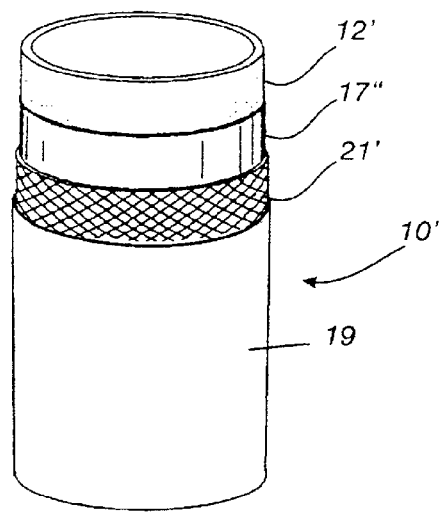
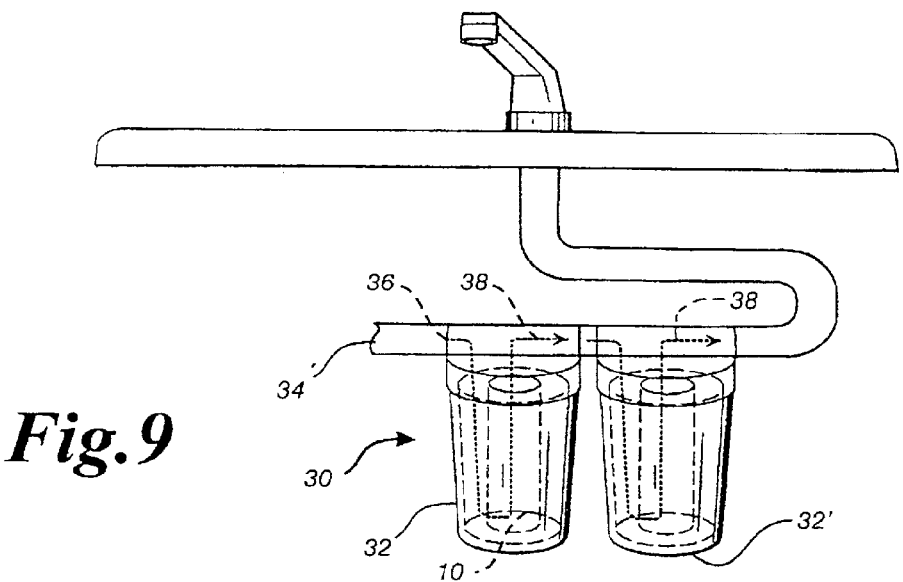

BACTERIOSTATIC FILTER CARTRIDGE

CROSS REFERENCE TO RELATED APPLICATIONS

This application is a continuation-in-part of U.S. patent application Ser. No. 09/181,358, filed Oct. 28, 1998, now U.S. Pat. No. 6,283,308, which is a continuation-in-part of U.S. patent application Ser. No. 08/877,080 filed Jun. 17, 1997, now U.S. Pat. No. 5,868,933 which is a continuation-in-part of U.S. patent application Ser. No. 08/573,067 filed Dec. 15, 1995, which issued as U.S. Pat. No. 5,762,797 on Jun. 9, 1998.

FIELD OF THE INVENTION

This invention relates generally to filters for the purification of liquids. In particular, the present invention relates to a bacteriostatic filter cartridge for use in a filtration system. The bacteriostatic filter cartridge is formed from layers of wound yarn and/or nonwoven melt blown web treated with an antimicrobial agent and wrapped about a porous core. The bacteriostatic filter cartridge is designed to remove particulates from water and prevent the growth of bacteria within the filter.

BACKGROUND OF THE INVENTION

In recent years, the public has become increasingly aware of the deteriorating quality of our nation's and the world's water supply. Pollutants, biological and toxic waste and other contaminants are being introduced into water supplies at an ever increasing rate, making such water supplies unfit for drinking and other necessary uses. For example, medical patients with low immunity are now being requested not to drink tap water, and disease and illnesses linked to poor quality drinking water have increased dramatically in recent years. This problem is especially significant outside the United States where water quality has deteriorated to an all time low, with the major source of such contamination primarily being bacterial in nature.

Contaminated water is a concern to industry as well. The semiconductor and pharmaceutical industries, among others, require ultra-pure water for their manufacturing processes. Therefore, a great amount of time, money and effort has been invested in developing systems to purify water. However, the systems that currently exist to purify water are generally too expensive or are not feasible in certain locations.

In addition to cost, all current filtration systems suffer from two recurring problems. The first is bacterial growth in the system. The second is fouling of the system due to overloads of contaminants. Either problem will exacerbate the other and reduce the overall efficiency of the system.

Of the current filtration systems available, reverse osmosis systems are the most common solutions for improving water quality through removal of particulates, dissolved solids and bacteria. Generally, these systems use a sediment removal filter in conjunction with activated carbon and a bacteriostatic membrane coated with oxides and halides of silver placed between the filter and the water outlet. Such a system is described in detail by Nishino in U.S. Pat. No. 3,872,013. The membrane will prevent certain bacteria from leaving the filter and will retard their growth on the surface of the membrane, but will not check bacterial growth on the activated carbon or the ability of bacteria to multiply and produce toxins. Other mechanical filters such as ceramic filter cartridges that filter out bacteria of about one micron in size also are ineffective in retarding bacterial growth as the bacteria are collected on the surface of the filter. If allowed to grow unchecked, the bacteria forms a film or slime on the filter which clogs the filter and further increase bacteria growth. Ceramic filters are required to be frequently cleaned by scraping for this reason.

Another type of biocidal reverse osmosis system is described in detail by Von Medlin in U.S. Pat. No. 5,269,919. Von Medlin teaches the use of a polyiodide resin that releases iodide upon contact with bacteria and viral organisms to combat bacterial growth, and uses granular metal alloys and activated carbon to remove iodides released in the water. If not removed, these iodides would be harmful to human beings. In fact, EPA "Policy on Iodine Disinfection", initially developed in 1973 and reaffirmed in 1982, is that iodine disinfection is for short-term only, whenever iodine-containing species remain in the drinking water.

Von Medlin is also representative of a "two-stage" filtration system that is sometimes employed to purify water. In this type of system two separate filtration stages are utilized. These stages are typically connected in series. However, multiple stages can be connected in parallel and in series or some combination thereof for large industrial applications or where the water to be filtered is heavily contaminated. One stage is typically used as a biocidal treatment unit as discussed above. The other stage(s) typically filter particulates and utilize reverse osmosis filters to remove salts and other dissolved materials from the water.

Another type of biocidal water filter is described in detail by Patrick, et al. in U.S. Pat. No. 5,762,797. Patrick teaches wrapping a microporous core with microporous membranes having a pore size distribution between 5.0 and $0.5\mu$ in conjunction with a tightly wound criss-cross wrapping of yarn, all of which may be treated with an antimicrobial agent. This type of filter is very effective at removing virtually all bacteria from water. However, these filters are best used as "finishing" filters for water that is already substantially free of contaminants.

If the water to be filtered is heavily contaminated several problems arise. For example, if a single filter cartridge or one "two-stage" system is employed to filter the water, the filter can quickly become fouled thereby severely restricting water flow. To remedy this problem, additional filters may be installed to create a multiple filter system. Such a system distributes particulate matter among several filters, thereby extending the time period between necessary filter maintenance and adding protection against sudden filter failure. Unfortunately, the creation of a multi-filter system using the filters described above will cause too large of a pressure drop across the system. Furthermore, if filters such as those described by Nishino or Von Medlin are used, the surface area upon which bacteria may multiply is greatly increased. Therefore, by adding extra filters to the system, bacteria contamination of the water to be filtered can actually increase.

It therefore can be seen that a need exists for an inexpensive and safe to use filter cartridge for a water filtration system that can filter particulate matter and large organisms and prevent bacterial and viral growth within the filter media, without releasing life harming toxins that have to be further filtered out and which does not unduly restrict water flow through the system.

SUMMARY OF THE INVENTION

Briefly described, the present invention comprises a bacteriostatic filter cartridge for a water filtration system. A bacteriostatic filter is a filter designed to more or less keep the concentration of bacteria in the effluent generally at or near the concentration of bacteria in the influent. This type of filter should be contrasted with a bacteriocidal filters that reduces the bacterial count by greater than 99% in the affluent as compared to that in the influent. A primary function of a bacteriostatic filter is to safely, effectively and economically filter particulates from drinking water and inhibit the growth of bacteria and other microorganisms within the filter to prevent an increase in the bacteria count of the effluent.

The filter cartridge includes an inner tubular-shaped perforated core of a metal, plastic or ceramic material. The core is generally wrapped with a yarn or melt blown web that has been impregnated or otherwise treated with an antimicrobial agent. The yarn or melt blown web is typically wound about the core to create a wrapping with very small openings through which water can travel. These openings or pores determine the size of the posticulate matter that is retained by the filters. The smaller the openings or pores denied, tighter the winding of the yarn or nonwoven around the core up to a point. Typically pores of up to 5 micron (nominal) size are possibly this technique.

If pores or openings smaller than 5 micron are desired, the bacteriostatic filter cartridge also can include a wet laid polyester membrane wrapped around the porous core prior to wrapping the yarn or melt blown web. A trilaminate composite membrane incorporating spunbonded outer layers sandwiching an inner layer of micron size melt blown fibers can be wrapped around the core in addition to the polyester membrane.

The filter cartridge also can include an extruded activated carbon core in place of a metal, plastic or ceramic core, with the activated carbon core having a nominal pore size of approximately $10.0\mu$. The activated carbon particles are mixed with a binder and an antimicrobial agent and extruded at a temperature where the binder melts and consolidates into a porous core. (See U.S. Pat. No. 5,331,037 by Kaslow).

The outer wrapped yarn or melt blown web section of the bacteriostatic filter is generally of sufficient thickness that the bacteriostatic filter cartridge can be tightly inserted into a cartridge housing, with minimal space between the bacteriostatic filter cartridge and the housing walls. The ends of the finished bacteriostatic filter are sealed with an antimicrobial polymer or resin, forming end caps at the opposite ends of the filter. This insures that the fluids being treated will pass through the entire filter before exiting the system.

The bacteriostatic filter cartridge is installed within a housing for a filtration system connected to a water supply. As water flows into the housing, water flows down and through the filter cartridge, and exits the housing through an outlet port. The filter cartridge of the present invention removes impurities from water flowing through the cartridge. Large impurities generally are removed by the yarn, melt blown web, and/or the polyester or trilaminate membranes. Microorganisms retained by the bacteriostatic filter, such as bacteria and viral contaminants, are forced into contact with the antimicrobial agent in the yarn and membranes and/or core thus inhibiting their growth. Thus it is possible to remove a substantial quantity of contaminants from water prior to a final filtering while at the same time preventing bacteria growth in the filtering system.

It is, therefore, an object of the present invention to provide a bacteriostatic filter cartridge that overcomes the above-discussed and other deficiencies of the prior art by providing a filter cartridge that substantially filters particulates from water and prevents the growth of bacterial and viral contaminants within the filter media.

A further object of the present invention is to provide a bacteriostatic filter cartridge that can be used in presently available filtration system housings including those used in reverse osmosis systems that will inhibit the growth of bacterial and viral contaminants and subsequent toxin production.

A further object of the present invention is to provide a bacteriostatic filter cartridge that substantially collects and removes particulate contaminants without creating a significant pressure drop across the filter system.

Another object of the present invention is to provide a bacteriostatic filter cartridge wherein nearly all of the bacteria retained by the bacteriostatic filter cartridge comes into contact with an antimicrobial agent and are deactivated.

Another object of the present invention is to provide a bacteriostatic filter having an activated carbon core impregnated with an antimicrobial agent.

Other objects, features, and advantages of the present invention will become apparent to one with skill in the art upon examination of the drawings and the detailed description.

BRIEF DESCRIPTION OF THE DRAWINGS

FIG. 1 is a side elevational view of a preferred embodiment of the present invention, with portions cut away.

FIG. 2 is a side elevational view of the filter cartridge of the present invention with end caps installed.

FIG. 3 is an end view of the filter cartridge of the present invention with an end cap installed.

FIG. 6 is a side view, of a polypropylene trilaminate membrane.

FIG. 7 is a side elevational view of an additional embodiment of the present invention with portions cut away.

FIG. 8 is a side elevational view of an additional embodiment of the present invention having an activated carbon core with portions cut away.

FIG. 9 is a schematic illustration of the filter cartridge of the present invention, showing the filter cartridge installed and used in an undersink filtration system.

DETAILED DESCRIPTION

Figure 4:
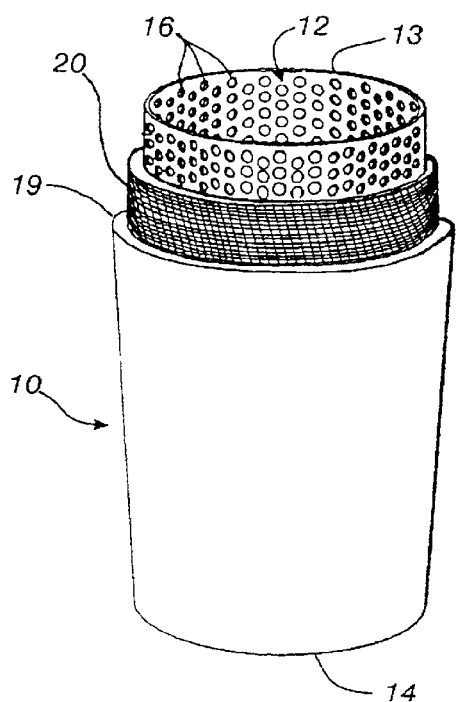
FIG. 4 is a side elevational view of a second embodiment of the present invention with portions cut away.

Referring now to the drawings in which like numerals indicate like parts throughout the several views, FIG. 1 illustrates a preferred embodiment of a bacteriostatic filter cartridge 10 constructed in accordance with the present invention. The bacteriostatic filter cartridge 10 includes a hollow central perforated core 12 having open ends 13 and 14, and which can be formed from plastic, paper, metal, or can be a ceramic candle material, which is inherently perforated. In the preferred embodiment shown in FIG. 1, the core is a porous polypropylene. The core is formed as a tube or cylinder approximately 5 to 30 inches in length and generally has a diameter of approximately 1 to 2 inches, although larger or smaller diameters can be used, if necessary. A series of pores or perforations 16 at least approximately 10 microns ($\mu$) in size or larger generally are formed through the core at spaced positions along its length.

The porous polypropylene core 12 is wrapped with yarn 18 treated with an antimicrobial agent. The yarn can be made of cotton, nylon, polypropylene, cellulose acetate, rayon, lyocell, acrylic, polyester, polyethylene or any mixture thereof. In a preferred embodiment shown in FIG. 1, the yarn 18 is 0.60 cotton count (cc) yarn 18. The yarn 18 contains polypropylene fiber between 0.3 denier per filament (dpf) to 10 dpf, the preferable range based on cost and performance being 1.5 dpf to 6 dpf. The polypropylene fiber was cut into 2 inch staple, then opened and carded and friction spun into a 0.60 cc yarn. The polypropylene fiber was impregnated with an antimicrobial agent during extrusion. The concentration of the antimicrobial agent in the fibers generally is between 50 to 20,000 ppm, preferably between 1000 ppm to 5000 ppm. The 0.60 cc yarn is tightly wound around the core in a criss-cross pattern to cover the core 12 completely and to give an effective pore size of 1–5μ.

Preferably, the antimicrobial agent used in the polypropylene fiber is practically insoluble in the water passing through and over the filter cartridge, and is safe, non-toxic, non-carcinogenic, non-sensitizing to human and animal skin and does not accumulate in the human body when ingested. Generally, therefore, the antimicrobial is a broad spectrum antimicrobial agent, i.e., it is equally effective against the majority of harmful bacteria encountered in water. For example, an antimicrobial agent such as 2,4,4'-trichloro-2'-hydroxydiphenol ether, or 5-chloro-2phenol (2,4dichlorophenoxy) commonly sold under the trademark MICROBAN®B, by Microban Products Co. typically will be used. However, it will be understood various other antimicrobial agents that are safe non-toxic and substantially insoluble in water can be used in the present invention.

The thickness of the criss-cross wrapped yarn 18 will determine the thickness of the bacteriostatic filter cartridge. Preferably, the criss-cross wrapped yarn is approximately ¼" thick, although the total thickness of the criss-cross wrapped yarn 18 can be of greater or lesser thickness, depending on the size of the filtration system housing, 19, in which the bacteriostatic filter cartridge is to be installed, to enable the bacteriostatic filter cartridge to fit tightly into a housing of a filtration system. Once the bacteriostatic filter has been wrapped to the desired finished thickness, the yarn is cut and the end is tucked under or otherwise secured to a previous strand to prevent the yarn from unraveling.

As shown in FIG. 2, end caps 22 are applied over the open ends 13 and 14 of the core and the wrapped yarn 18 to seal the ends of the bacteriostatic filter cartridge. The end caps 22 generally comprise a polyvinyl chloride (PVC) plastisol material containing an antimicrobial agent such as MICROBAN®B. The plastisol is poured in a liquid form into a shallow mold having an opened inside tube. A first end of the bacteriostatic filter cartridge 10 is then set into the mold containing the plastisol liquid, heated to a recommended temperature, for example 260° F., for approximately seven minutes or until the plastisol has sufficiently permeated and set in the yarn 18 at the ends of the filter. The bacteriostatic filter cartridge is removed and its opposite or second end is dipped into the plastisol liquid heated and set as above. The plastisol liquid is allowed to cool and solidify over the ends of the bacteriostatic filter cartridge, whereupon the plastisol adheres to the fibrous yarn 18 to seal the ends of the bacteriostatic filter cartridge, while still leaving the center of the cartridge open as shown in FIG. 3.

In an alternative embodiment, preformed end caps may be used in place of the end caps formed from the plastisol liquid. Such preformed caps generally are formed from a plastic material, such as polypropylene, treated with an antimicrobial agent. The caps are formed to ensure sealing of the ends of the microporous membrane and applied to the ends of the bacteriostatic filter cartridge, preferably with an antimicrobial adhesive.

The end caps seal and cover the ends of the criss-cross wrapped yarn 18 at each end thereof. This forces the water or other fluid being filtered through the filtration system to pass through the sides of the bacteriostatic filter cartridge to ensure that the water or other fluid will pass through and contact the criss-cross wrapped yarn 18 so that contaminants of at least 1.0 micron or larger are trapped and removed from the flow of water passing through the filter cartridge. The antimicrobial agent in the yarn 18 also works to inhibit the growth of bacteria and other microorganisms within the bacteriostatic filter.

In an alternative embodiment shown in FIG. 4, the wrapped yarn 18 is replaced by a melt blown web 20 of polymer. The polymer may be selected from the group consisting of nylon, polypropylene, cellulose acetate, rayon, lyocell, acrylic, polyester, polyethylene and mixtures thereof. The alternative embodiment shown in FIG. 4, polypropylene fibers were impregnated with MICROBAN®B during extrusion and blown into a continuous web having the following properties.

| | |
|---|---|
| Thickness | 20 mil |
| Minimum pore size | 5 micron |
| Maximum pore size | 40 micron |
| Mean pore size | 12 micron |
| Frazier Permeability | 38 CFM |

The concentration of the antimicrobial agent in the fibers generally is between 50 to 20,000 ppm, preferably between 1000 ppm to 5000 ppm. The melt blown web 20 was then wound around a porous polypropylene core 12 to produce a bacteriostatic filter. End caps are then added as discussed previously.

Figure 5:
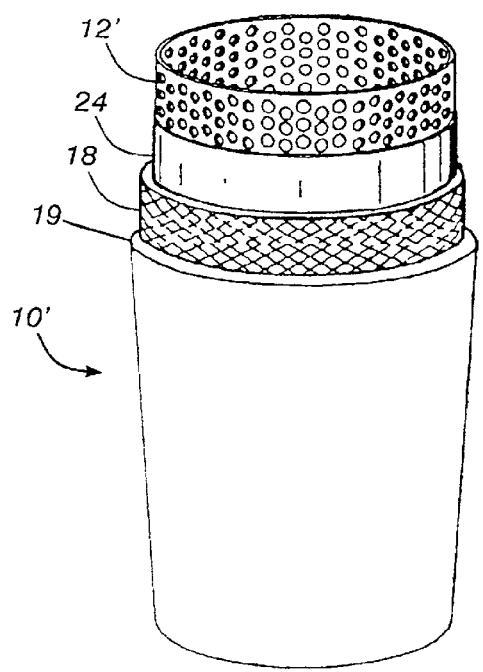
FIG. 5 is a side elevational view of the second embodiment of the present invention with portions cut away.

In another alternative embodiment, which is shown in FIG. 5, a porous polypropylene core 12 was covered with three wrappings of a wet laid polyester membrane 24 manufactured by Veratec Corporation. Preferably the width of the wet laid polyester membrane 24 is slightly wider than the height of polypropylene core 12 so that the polyester membrane may slightly overlap the ends of core 12. The purpose of polyester membrane 24 is to further narrow the pore distribution in the bacteriostatic filter and to reduce the effective pore diameter of the bacteriostatic filter. A MICROBAN®B treated melt blown web 20 or criss-crossed yarn 18 may be wound around the polyester membrane 24. PVC end caps 22 may be placed at either end to secure the polyester membrane 24 and the treated yarn 18 or melt blown web 20. The polyester membrane 24 used in the conducted tests exhibited the following properties.

| | |
|---|---|
| Weight | 4.3 oz per sq. yard |
| Thickness | 4.2 mil |
| Bubble point | 0.29 psi |
| Frazier Permeability | 4.3 CFM |
| Mean Flow pore diameter | 11.2 micron |
| Smallest pore diameter | 1.87 micron |

The polyester membrane may also be treated with MICROBAN®B if desired.

In a further embodiment shown in FIG. 6, following the polyester membrane 24 described above, are two wrappings of a MICROBAN®B treated trilaminate composite membrane 26. Preferably, the trilaminate composite membrane 26 has a width that is slightly larger than the height of core 12 so that the edges of trilaminate composite membrane 26 slightly extend over the ends 13 and 14 of core 12 so that the edges may be tucked around ends 13 and 14 and secured by end caps 22. Trilaminate composite membrane 26 is formed by sandwiching an inner layer of micron size melt blown fibers 28 between two spunbonded outer layers of polypropylene 30. FIG. 7. The trilaminate composite membrane 26 used in testing exhibited the following properties.

| | |
|---|---|
| Weight | 2.6 oz. per sq. yard |
| Thickness | 19 mil |
| Frazier Permeability | 50 CFM |
| Mean Pore Size | 1 micron |

The purpose of this membrane is to further reduce the effective pore size and to protect the polyester membrane 24 from accumulation of bacteria. Trilaminate composite membrane 26 converts the filter to an absolute 1 micron particle filter, meaning that 100% of the particles of 1 micron diameter will be filtered by this construction.

A layer of yarn 18 or melt blown web 20 is wrapped around the trilaminate composite membrane 26. PVC endcaps 22 may then be placed at either end of the filter as described above. Alternatively, plastic end caps may be attached using an EVA adhesive. It should be understood by those skilled in the art that each of the wrappings disclosed above (i.e. criss-crossed yarn, melt blown web, polyester membrane, and composite membrane) can be used alone or in combination with any of the other wrappings.

In an additional embodiment shown in FIG. 8, the perforated polypropylene core 12 (FIG. 1) is replaced with an extruded core of activated carbon 12' treated with an antimicrobial agent. Activated carbon core 12' may then be wrapped with yarn 18, melt blown web 20, polyester membrane 24, trilaminate composite membrane 26 or any combination thereof in the manner previously described. In the embodiment shown in FIG. 8, the activated carbon core 12' is wrapped with a polyester membrane 24 and criss-crossed yarn 18. The resulting bacteriostatic filter may then be end capped with PVC plastisol as previously described. Alternatively, plastic end caps may be attached using an EVA adhesive.

Activated carbon generally is used in water treatment for removal of offensive tastes, odor, chlorine, dissolved organics and removal of certain heavy metals in combination with special media. These special media may consist of micronized $MnO_2$ or specialty product such as ATS™ or ATC™ made by Englegard to remove lead and other heavy metals. Activated carbon is, however, also a source of nutrients for heterotrophic bacteria, which tends to result in increased growth and bacterial activity within the filter. Increased bacterial growth causes the carbon to become fouled, resulting in a high pressure drop in the water flow and the possible multiplication and spreading of infectious bacteria.

In the present invention, however, the activated carbon core 12' is formed having an antimicrobial agent impregnated therein, which inhibits bacterial growth. The process of extruding the activated carbon cores is described in U.S. Pat. Nos. 5,189,092, 5,249,948 and 5,331,037. The antimicrobial treated activated carbon core 12' is formed by first homogeneously mixing an antimicrobial agent with a thermoplastic binder that melts and binds with carbon particles when heated in a homogeneous mixture. The antimicrobial agent preferably is the same antimicrobial material as that used to treat the yarn at the filter, typically a 2,4,4'-trichloro-2'-hydroxy diphenol ether or 5-chloro-2-phenol (2,4-dichlorophenoxy) compound, that is commonly manufactured and sold under the trademark "MICROBAN®B" by Microban Products Company, Huntersville, N.C., or an equivalent antimicrobial agent that is insoluble in water. It is important that the antimicrobial agent not leach into the water being filtered during the filtration process. The above-described antimicrobial agents or their equivalent, which are insoluble in water, are safe to use in the water filtration process carried out by the present invention.

Typically, the thermoplastic binder with which the antimicrobial agent is mixed typically is a low density polyethylene powder or a similar binder material, such as polypropylene, polyester, fluropolymer, nylon or aramids, that easily and substantially completely melts and binds with carbon particles. U.S. Pat. No. 5,331,037 describes many other thermoplastic binders that can be used in the extrusion of activated cores. Typically, the concentration of the MICROBAN®B antimicrobial agent applied with the binder is in the range of approximately 50–20,000 ppm (parts per million) based upon the weight of the activated carbon being treated. Preferably, a concentration of 1,000–5,000 ppm of the MICROBAN®B antimicrobial agent is used based on the weight of the activated carbon. The antimicrobial treated binder is added to granular activated carbon, being uniformly mixed therewith. The entire mixture thereafter is heated to a temperature of approximately 350°–450° F. It will also be understood that when other polymeric binder materials are used, typically the mixtures are heated to temperatures above the melting point for the specific polymers being used. In general, the entire mixture is comprised of 5%–30% binder, typically 20% being the desired level, and the remaining portion comprising activated carbon granules. After the mixture has been heated to its melting point, the mixture is then extruded into a desired shape to form antimicrobial treated activated carbon core as shown in FIG. 8.

Operation

In use, the bacteriostatic filter cartridge 10 typically is mounted within the housing of a conventional water filtration system such as an undersink system 30 as shown in FIG. 9. In the system of FIG. 9, the filter cartridge 10 is fitted snugly inside a filter cartridge housing 32 and the filtration system 30 is connected to a water source at the inlet end of the housing. The water is supplied to the filtration system at a desired flow rate and flows into the upstream or inlet end 34 of the housing as indicated by arrows 36. The water flows through the filter cartridge and out of the housing, whereupon the bacteriostatic filter cartridge 10 traps and removes particulate contaminants within the water flow to clean and purify the water flow before the water flow exits the housing through an outlet port 38. The activated carbon core of this filter cartridge in addition removes chlorine taste and odor as well as certain dissolved organic components. An additional filter cartridge housing 32' can be mounted downstream from the housing 32 for further cleaning of the water flow.

During use of the bacteriostatic filter cartridge 10 of the present invention, the flow of water, as indicated in FIG. 9 passes through the sides of the bacteriostatic filter cartridge and out the open ends of the core. It will, however, be understood by those skilled in the art that the bacteriostatic filter cartridge of the present invention functions equally well if the water flow were to be reversed so as to flow in through the ends of the cartridge and out through the sides of the cartridge, without affecting the ability of the cartridge to trap and retard particulates within the flow. Under the alternative flow conditions, the sequence of membrane and antimicrobial yarn may have to be altered.

Several tests were conducted in the course of developing the various embodiments of the invention. First, the ability of the treated yarn and the melt blown web to inhibit the growth of bacteria was explored. It was determined that both the treated yarn and the melt blown web were quite effective in retarding the growth of bacteria. It was shown that the treated yarn exhibited a zone of inhibition of 4 mm while the melt blown web exhibited a zone of inhibition of 10 to 12 mm.

Tests were also conducted to confirm the inhibition of bacterial growth by the treated activated carbon core. In one test that was conducted, several samples of MICROBAN®B treated activated carbon were immersed in 100 cc of spiked deionized ("DI") water containing about 5000 colonies of *E. coli* per cc. The following results were obtained.

| Sample | Core Wight (grams) | Date Started | Dated Tested | Colonies per cc |
|---|---|---|---|---|
| ANALYSIS: | | | | |
| Background | N/A | 11/13 | 11/13 | 5090 |
| 24 hours | 28.7834 | 11/13 | 11/14 | 3810 |
| 48 hours | 25.2915 | 11/13 | 11/15 | 4150 |
| 120 hours | 26.1046 | 11/13 | 11/18 | 260 |

The bacterial inhibition demonstrated above should be contrasted with the bacterial growth demonstrated when untreated activated carbon was brought into contact with bacteria. The following results were obtained when several samples of untreated activated carbon were immersed in 100 cc of spiked DI water containing about 5000 colonies of *E. Coli* per cc.

| Sample | Core Wight (grams) | Date Started | Dated Tested | Colonies per cc |
|---|---|---|---|---|
| ANALYSIS: Total Coliform: | | | | |
| Background | N/A | 1/21 | 1/21 | 6620 |
| 24 hours | 23.6381 | 1/21 | 1/22 | 8380 |
| 48 hours | 24.0788 | 1/21 | 1/23 | 9140 |
| 120 hours | 22.5115 | 1/21 | 1/26 | 11600 |

| Sample | Core Wight (grams) | Date Started | Dated Tested | Colonies per cc |
|---|---|---|---|---|
| ANALYSIS: Staphylococcus: | | | | |
| Background | N/A | 1/21 | 1/21 | 5900 |
| 24 hours | 22.7572 | 1/21 | 1/22 | 9050 |
| 48 hours | 21.2508 | 1/21 | 1/23 | 10850 |
| 120 hours | 23.0548 | 1/21 | 1/26 | 12400 |

Figure 10:
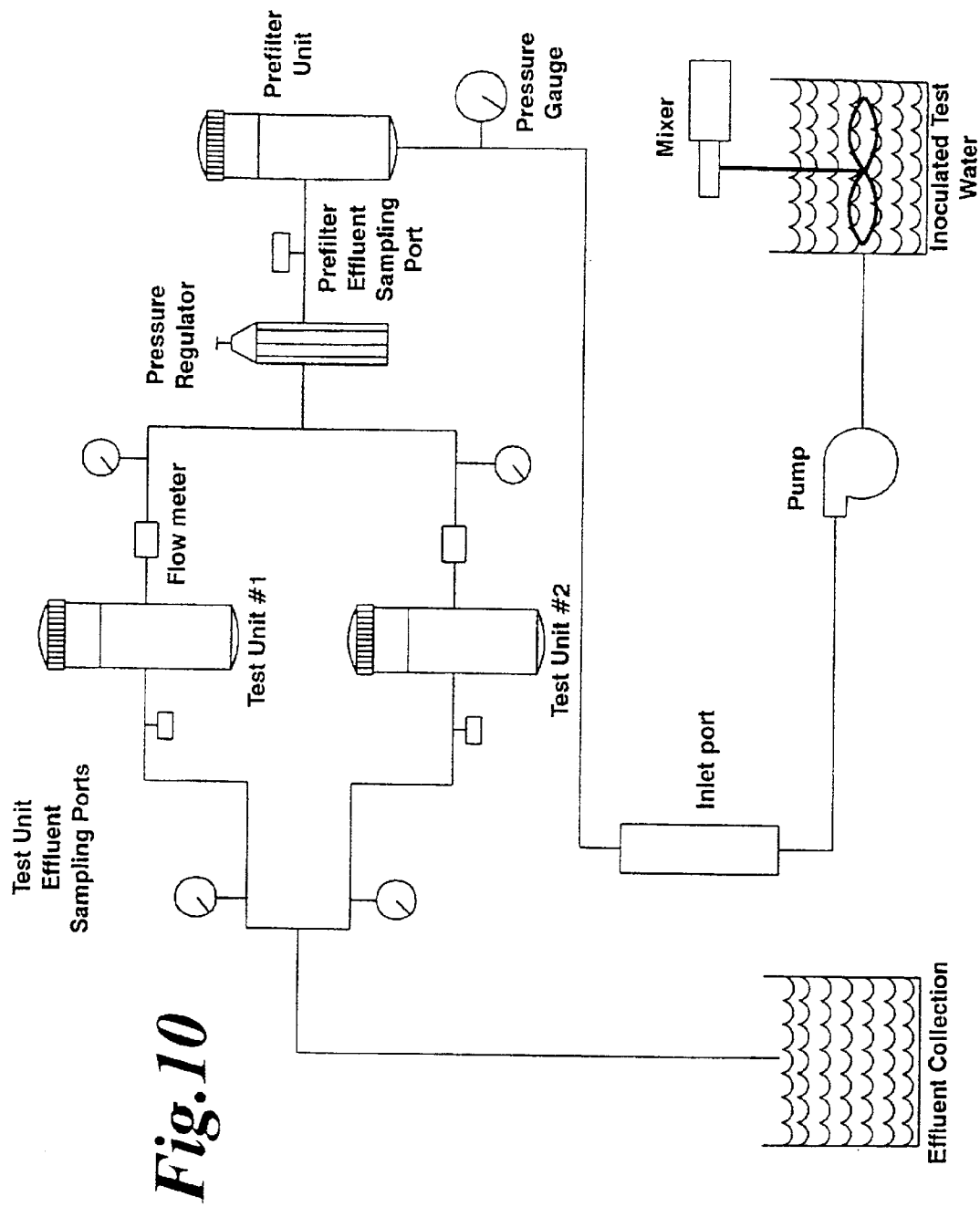
FIG. 10 is a schematic illustration of the testing apparatus used in gathering the data.

Several tests were also conducted to confirm the bacteriostatic nature of the filters. FIG. 10 shows the testing apparatus used to test the bacteriostatic filters. During testing, water flowed through the test apparatus at the rate of 2 gpm. About 0.5 million CFU of Coliform bacteria were injected into the inlet port with a peristaltic pump to create a filter influent bacteria concentration of between 40,000 to 50,000 CFU per ml. The effluent was analyzed for the bacterial content using standard Total Plate Count. The effluent was also analyzed for the presence of dissolved MICROBAN®B by chromatography with a sensitivity of 50 ppb. No MICROBAN®B was detected.

The following test results document the effluent concentration of bacteria for a bacteriostatic filter constructed of a porous polypropylene core and wound with a criss-cross pattern of 0.60 cc yarn containing MICROBAN®B.

| Sample | Total Coliform Colonies per cc |
|---|---|
| ANALYSIS: 2 gal. Per minute flow rate - Tap Water | |
| Inject 10 CC (Ca. 0.5 million CFU) 5 min. after 1st injection | 8200 |
| Inject 10 cc (Ca. 0.5 million) 5 min. after 2nd injection | 9800 |
| Inject 10 cc (ca. 0.5 million) 5 min. after 3rd injection | 7600 |
| Inject 10 cc (ca. 0.5 million) 5 min. after 4th injection | 6800 |
| Inject 10 cc (ca. 0.5 million) 5 min. after 5th injection | 7100 |
| Inject 10 cc (Ca. 0.5 million) 5 min. after 6th injection | 5800 |
| 10 min. after 6th injection | 6000 |
| Exterior of Filter: | |
| After 48 hours | 5200 |
| After 72 hours | 5500 |
| After 96 hours | 4800 |

In all cases, the effluent concentration never exceeded the influent concentration of 40,000 to 50,000 CFU per ml. Furthermore, the water samples analyzed exterior to the filter in the housing did not show any increase in the level of bacteria even after 96 hours. The effluent was then analyzed for the presence of dissolved MICROBAN®B by chromatography with a sensitivity of 50 ppb. No MICROBAN®B was detected.

The following test results document the effluent concentration of bacteria for a bacteriostatic filter constructed of a porous polypropylene core about which is wound with a melt blown web treated with MICROBAN®B.

| Sample | Total Coliform Colonies per cc |
|---|---|
| ANALYSIS: 2 gal. Per minute flow rate - Tap Water | |
| Inject 10 CC (Ca. 0.5 million 5 min. after 1st injection | 8500 |
| Inject 10 cc (Ca. 0.5 million) 5 min. after 2nd injection | 5900 |
| Inject 10 cc (ca. 0.5 million) 5 min. after 3rd injection | 6200 |
| Inject 10 cc (ca. 0.5 million) 5 min. after 4th injection | 6800 |
| Inject 10 cc (ca. 0.5 million) 5 min. after 5th injection | 5000 |
| Inject 10 cc (Ca. 0.5 million) 5 min. after 6th injection | 5500 |
| Exterior of Filter: | |

-continued

ANALYSIS:
2 gal. Per minute flow rate - Tap Water

| Sample | Total Coliform Colonies per cc |
|---|---|
| After 48 hours | 4300 |
| After 72 hours | 4600 |
| After 96 hours | 4200 |

Once again, the concentration of bacteria in the effluent never exceeded the influent concentration of 40,000 to 50,000 CFU per ml. Once again, there was no increase in the level of bacteria in the filter after 96 hours.

What is claimed is:

1. A bacteriostatic filter cartridge, comprising an inner perforated core member and a yarn wound about said core in a criss-cross pattern, where at least one of the group consisting of said inner perforated core member and said yarn is impregnated with a non-leaching antimicrobial agent selected from the group consisting of 2,4,4'-trichloro-2-hydroxy diphenol ether and 5-chloro 2 phenol (2,4 dichlorophenoxy) compounds.

2. The bacteriostatic filter cartridge of claim 1, wherein said core member is selected from the group consisting of activated carbon, plastic, paper, metal and ceramic.

3. The bacteriostatic filter cartridge of claim 1 wherein said yarn is comprised of at least one member of the following group consisting of cotton, nylon, polypropylene, cellulose acetate, rayon, lyocell, acrylic, polyester, polyethylene and mixtures thereof.

4. The bacteriostatic filter cartridge of claim 1 wherein said criss-crossed wrapped yarn forms a filter with an effective pore size between 1 micron and 5 microns.

5. A bacteriostatic filter cartridge, comprising an inner perforated core member and a melt blown web wrapped about said core, where at least one of the group consisting of said inner perforated core member and said melt blown web is impregnated with a non-leaching antimicrobial agent selected from the group consisting of 2,4,4'-trichloro-2-hydroxy diphenol ether and 5-chloro 2 phenol (2,4 dichlorophenoxy) compounds.

6. The bacteriostatic filter cartridge of claim 5, wherein said core member is selected from the group consisting of activated carbon, plastic, paper, metal and ceramic.

7. The bacteriostatic filter cartridge of claim 5, wherein said melt blown web is made from a polymer selected from the group consisting nylon, polypropylene, cellulose acetate, rayon, lyocell, acrylic, polyester, polyethylene and mixtures thereof.

8. The bacteriostatic filter cartridge of claim 5 wherein said melt blown web exhibits a minimum pore size of about 5 microns and a maximum pore size of about 40 microns with a mean pore size between 5 microns and 20 microns.

9. A bacteriostatic filter cartridge, comprising an inner perforated core member, a wet laid polyester membrane wrapped around said core member, a composite membrane wrapped around said polyester membrane and a criss-crossed layer of yarn wrapped around said composite membrane where at least one of the group consisting of said inner perforated core member, said wet laid polyester membrane, said composite membrane and said yarn is treated with a non-leaching antimicrobial agent.

10. The bacteriostatic filter cartridge of claim 9, wherein said core member is selected from the group consisting of activated carbon, plastic, paper, metal and ceramic.

11. The bacteriostatic filter cartridge of claim 9 wherein said yarn is comprised of at least one member of the following group consisting of cotton, nylon, polypropylene, cellulose acetate, rayon, lyocell, acrylic, polyester, polyethylene and mixtures thereof.

12. The filter cartridge of claim 9 wherein said layer of criss-crossed yarn is replaced by a melt blown web.

13. The filter cartridge of claim 12 wherein said melt blown web is treated with a non-leaching antimicrobial agent.

14. The bacteriostatic filter cartridge of claim 13 wherein said antimicrobial agent is selected from the group consisting of 2,4,4-trichloro-2-hydroxy diphenol ether and 5-chloro-2phenol(2,4 dichlorophenoxy) compounds.

15. The bacteriostatic filter cartridge of claim 12, wherein said melt blown web is made from a polymer selected from the group consisting of nylon, polypropylene, cellulose acetate, rayon, lyocell, acrylic, polyester, polyethylene and mixtures thereof.

16. The bacteriostatic filter cartridge of claim 9 wherein said antimicrobial agent is selected from the group consisting of 2,4,4-trichloro-2-hydroxy diphenol ether and 5-chloro-2phenol(2,4 dichlorophenoxy) compounds.

17. A bacteriostatic filter cartridge comprising an inner perforated core member wrapped by at least one member of the group consisting of a criss-crossed pattern of yarn, a wet laid polyester membrane, a composite membrane and a melt blown web, where at least one member of the group consisting of said inner perforated core member, said yarn, said polyester membrane and said melt blown web is treated with a non-leaching antimicrobial agent.

* * * * *